(12) United States Patent
Escalante-Semerena et al.

(10) Patent No.: US 7,531,337 B2
(45) Date of Patent: May 12, 2009

(54) METHOD OF CONTROLLING ACETYLATION OF METABOLIC ENZYMES

(75) Inventors: Jorge C. Escalante-Semerena, Madison, WI (US); Vincent J. Starai, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 174 days.

(21) Appl. No.: 10/456,097

(22) Filed: Jun. 6, 2003

(65) Prior Publication Data

US 2003/0232782 A1 Dec. 18, 2003

Related U.S. Application Data

(60) Provisional application No. 60/387,557, filed on Jun. 7, 2002.

(51) Int. Cl.
*C12Q 1/48* (2006.01)
*C12N 9/10* (2006.01)
*G01N 33/53* (2006.01)
*C07H 21/04* (2006.01)

(52) U.S. Cl. .................. 435/193; 435/7.6; 536/23.2
(58) Field of Classification Search ............... 435/183, 435/23.3, 6
See application file for complete search history.

(56) References Cited

OTHER PUBLICATIONS

Starai et al. Sir2-dependent activation of acetyl-CoA synthetase by deacetylation of active lysine. Science. Dec. 20, 2002;298(5602):2390-2.*
Ampe et al. Acetate utilization is inhibited by benzoate in Alcaligenes eutrophus: evidence for transcriptional control of the expression of acoE coding for acetyl coenzyme A synthetase. J Bacteriol. Oct. 1995;177(20):5826-33.*
McClelland et al. GenBank Accession No. AE008820, *Salmonella typhimurium* LT2, section 124 of 220 of the complete Genome, created Oct. 25, 2001.*
McClelland et al. UniProt No. Q8ZMX2, Putative acetyl-CoA synthetase, created Mar. 1, 2002.*
Lee et al. (J Biochem (Tokyo), Identification of active site residues in *Bradyrhizobium japonicum* acetyl-CoA synthetase, Dec. 2001; 130(6): 807-13).*
Smith, J. S. et al., Proc. Nat'l. Acad. Sci. 97, 6658-6663 (2000).
Pfeifer, B. A. et al., Science 291, 1790-1792 (2001).
Tsang, A. W. et al., J. Biol. Chem. 273, 31788-31794 (1998).
Moazed, D., Curr Opin Cell Biol 13, 232-238 (2001).
Horswill, A. R. and Escalante-Semerena, J. C., Biochemistry 41, 2379-2387 (2002).
Bell, S. D. et al., Science 296, 148-151 (2002).
Starai, V. J., et al., Genetics 163, 545-555 (2003).
McClelland, M., et al., "Complete genome sequence of *Salmonella enterica serovar* Tryphimurium LT2," Nature 413:852-855 (2001).
Parkhill, J., et al. "Complete genome sequence of a multiple drug resistant *Salmonella enterica serovar* Typhi CT18," Nature 413:848-849 (2001).

* cited by examiner

*Primary Examiner*—Nashaat T Nashed
*Assistant Examiner*—Iqbal H Chowdhury
(74) *Attorney, Agent, or Firm*—Quarles & Brady, LLP

(57) ABSTRACT

A method for modulating the activity of an AMP-forming enzyme (AFE) is disclosed. The method is based upon the novel observation that the activity of these enzymes is controlled by acetylation of the enzymes to inactivate them and de-acetylation of the enzymes to re-activate them. The acetylation of the enzyme occurs at a characteristic lysine residue. Various polypeptides, nucleic acids and other molecules that are related to modulating the AFE activity are also disclosed. Further disclosed are methods of modulating cellular acetyl-CoA or propionyl-CoA levels in bacterial hosts, methods of identifying agents that can modulate the activity of AFE acetylases, and methods of identifying AFE mutants that are insensitive to acetylation regulation.

2 Claims, 5 Drawing Sheets

FIG. 3

| | | | | | | | | | | | | | | | | | |
|---|---|---|---|---|---|---|---|---|---|---|---|---|---|---|---|---|---|
| Acs | 600 | D | S | L | | L | K | T | R | S | G | K | I | M | R | 612 | (SEQ ID NO:12) |
| PrpE | 583 | S | Q | L | | L | K | T | R | S | G | K | M | L | R | 595 | (SEQ ID NO:13) |
| Acs2p | 628 | R | D | L | | R | R | T | R | S | G | K | I | M | R | 640 | (SEQ ID NO:14) |
| luciferase | 520 | D | E | V | P | K | G | T | L | T | G | K | L | D | A | 532 | (SEQ ID NO:15) |
| GrsA | 508 | D | K | M | P | L | T | L | A | N | G | K | V | D | R | 520 | (SEQ ID NO:16) |
| CepA A1 | 470 | D | A | L | P | L | T | T | H | N | G | K | I | D | R | 482 | (SEQ ID NO:17) |
| CepA A2 | 1490 | D | A | L | P | L | T | A | T | N | G | K | V | D | R | 1502 | (SEQ ID NO:18) |
| CepA A3 | 3022 | D | A | L | P | L | T | A | H | N | G | K | L | D | R | 3034 | (SEQ ID NO:19) |
| cda PSI A1 | 1059 | P | R | L | P | V | T | L | L | N | G | K | L | D | T | 1071 | (SEQ ID NO:20) |
| cda PSI A2 | 2169 | D | V | L | P | L | T | T | P | N | G | K | L | D | R | 2181 | (SEQ ID NO:21) |
| cda PSI A3 | 3234 | D | A | L | P | L | T | T | P | N | G | K | L | D | R | 3246 | (SEQ ID NO:22) |
| cda PSI A4 | 4731 | D | A | L | P | L | T | T | P | N | G | K | L | D | R | 4743 | (SEQ ID NO:23) |
| cda PSI A5 | 5771 | D | A | L | P | L | T | T | P | N | G | K | L | D | R | 5783 | (SEQ ID NO:23) |
| cda PSI A6 | 6853 | D | A | L | P | L | T | T | P | N | G | K | L | D | R | 6865 | (SEQ ID NO:23) |

FIG. 4

SEQ ID NO:1 atgagccagcaaggactggaagcgctactgcgaccaaaatcgatcgcggtgattggcgcatcaatgaagccccaccgcgc
gggttacctgatgatgcgtaacttgttggcgggcggattcaatggccccgtccttcccgtgacgcccgcctggaaagccg
ttttaggcgtcatggcctggccggatatcgccagtcttcctttcaccccgatctggctatttatgcactaacgccagc
cgtaacctggcgttactggacgcgcttggcgcgaaagggtgtaaaacgtgcattatcctttctgctcccacgtcgcaaca
tgaagaacttcttgcctgtgcccggcattataaaatgcgtctgctgggtccaaacagtcttgggctcctcgcgccgtggc
aagggctgaatgccagcttttctcccgtcccgattaaacagggcaagctcgcttttatttcccagtctgccgccgtgtcc
aatactattcttgactgggcgcaacagcgtgaaatgggcttttcctactttatcgcgctgggcgatagcctggatattga
tgtcgatgaactactggactatctggcgcgcgacagcaagaccagcgcgattttgctctatctggaacagttaagcgacg
cccgccgttttgtttccgccgcccgtagcgcttcacgtaacaaaccgattctggtgattaaaagcggccgaagcccggca
gcccagcgtttacttaataccagcgcgggaatggaccctgcgtgggatgcggccatccagcgcgcaggcctgctgcgagt
ccaggatacgcacgagcttttttccgccgtcgaaacactgagccatatgcgtccgctacgcggcgacagactgatgatca
tcagcaatggcgccgcgcctgccgcgctggcgttagatgagttgtggtcgcgtaacggcaagctggcgacgttagcgaa
gagacctgcctgcaactacggcaggcgcttcccgcgcacatagatattgccaatccgctggatctgtgtgatgacgccag
cagcgaacattacgtcaaaacgctggatatcctgctcgccagtcaggattttgacgcgcttatggttatccactctccca
gcgctgccgcgccgggtacagaaagcgcccatgctctgatcgagacgattaagcgccaccccagaggcaagtttgttacg
ctgctgacaaactggtgcggcgagttctcgtctcaggaggcaagacggctattcagcgaagccggattaccaacctaccg
tacgccggaaggcacgattaccgcgtttatgcatatggtggaataccggcgtaaccagaagcaactgcgggaaacgccag
cgttgccgagtaacctgacgtccaataccgctgaggcgcataatctgttacagcgggcgattgcggaaggcgccgcctca
ctggatacccatgaagtacagccgattttacacgcctatgggctgcacacgctcccaacctggattgccagcgacagcgc
tgaagcggtgcatattgccgaacagata<mark>tgtctcaaagcgctctctgcgtctgtcgcgcgtccagaaactggaacgtga
tcaatctgtgtgctcgtttctcacgtgatgctgtcgtgtatatctgtcacctctggtcgtcgagcacgatcc</mark>gcatggctaaccgcgcc<mark>ggcgcgcaggagcttcgtg
gctgctcgagcacgatcc</mark>ggtgtttggtcctttgattatgttgggtgaaggcggcgtagagtggcgtccggaagagcagg
ctgtcgcgctgccgccgctcaacatgaacctggcgcgctatctggtgattcagggcattaaacagcggaaaattcgc
gcccgtagcgcgctgcgtccgctggatattgtcggtttaagccaattgctggtccaggttcaaacctgattgtcgactg
cccggaaattcagcgtctggatatccatccgctgctggcttccgccagtgagtttaccgcgctggatgtgacgctggata
ttgccccgtttgatggcgataacgaaagtcgacttgcggtacgccctatccccaccagcttgaagagtgggtggagatg
aaaaatggcgatcgctgcctgttccgtcctatcctgccggaagatgagccccaactgcgacaattcatcgcacaggtcac
caaagaggatctttactaccgttatttcagcgagatcaacgaattcacccatgaagatttagccaacatgacgcagatcg
actacgatcgagaaatggcctttgtggccgtgaggcggatggacaatgctgaagagatcctcggcgtaacgcgcgcgatc
tccgatcctgacaacgtagatgccgaatttgccgtattggtgcgttcagatctcaaagggttgggtttaggacgccgttt
aatggagaaattgattgcctatactcgcgatcacggattgaagcggctgaacggtattacgatgccaaacaatcgcggca
tggtcgcgctggccagaaaactgggatttcaggtcgatattcagctcgaagagggcatcgtgggattgacgctgaatctg
gccaaatgtgatgaatcgtga

```
SEQUENCE LISTING

<160> NUMBER OF SEQ ID NOS: 24

<210> SEQ ID NO 1
<211> LENGTH: 2661
<212> TYPE: DNA
<213> ORGANISM: Salmonella typhimurium

<400> SEQUENCE: 1
atgagccagc aaggactgga agcgctactg cgaccaaaat cgatcgcggt gattggcgca      60
tcaatgaagc cccaccgcgc gggttacctg atgatgcgta acttgttggc gggcggattc     120
aatggccccg tccttcccgt gacgcccgcc tggaaagccg ttttaggcgt catggcctgg     180
ccggatatcg ccagtcttcc tttcaccccc gatctggcta ttttatgcac taacgccagc     240
cgtaacctgg cgttactgga cgcgcttggc gcgaaagggt gtaaaacgtg cattatcctt     300
tctgctccca cgtcgcaaca tgaagaactt cttgcctgtg cccggcatta taaaatgcgt     360
ctgctgggtc aaacagtctg tgggctcctc gcgccgtggc aagggctgaa tgccagcttt     420
tctcccgtcc cgattaaaca gggcaagctc gcttttattt cccagtctgc cgccgtgtcc     480
aatactattc ttgactgggc gcaacagcgt gaaatgggct tttcctactt tatcgcgctg     540
ggcgatagcc tggatattga tgtcgatgaa ctactggact atctggcgcg cgacagcaag     600
accagcgcga ttttgctcta tctggaacag ttaagcgacg cccgccgttt tgtttccgcc     660
gcccgtagcg cttcacgtaa caaaccgatt ctggtgatta aagcggccg aagcccggca     720 gcccagcgtt tacttaatac cagcgcggga atggaccctg cgtgggatgc ggccatccag     780
cgcgcaggcc tgctgcgagt ccaggatacg cacgagcttt tttccgccgt cgaaacactg     840
agccatatgc gtccgctacg cggcgacaga ctgatgatca tcagcaatgg cgccgcgcct     900
gccgcgctgg cgttagatga gttgtggtcg cgtaacggca agctggcgac gttgagcgaa     960
gagacctgcc tgcaactacg gcaggcgctt cccgcgcaca tagatattgc caatccgctg     1020
```

-continued

```
gatctgtgtg atgacgccag cagcgaacat tacgtcaaaa cgctggatat cctgctcgcc   1080
agtcaggatt ttgacgcgct tatggttatc cactctccca gcgctgccgc gccgggtaca   1140
gaaagcgccc atgctctgat cgagacgatt aagcgccacc ccagaggcaa gtttgttacg   1200
ctgctgacaa actggtgcgg cgagttctcg tctcaggagg caagacggct attcagcgaa   1260
gccggattac caacctaccg tacgccggaa ggcacgatta ccgcgtttat gcatatggtg   1320
gaataccggc gtaaccagaa gcaactgcgg gaaacgccag cgttgccgag taacctgacg   1380
tccaataccg ctgaggcgca taatctgtta cagcgggcga ttgcggaagg cgccgcctca   1440
ctggataccc atgaagtaca gccgatttta cacgcctatg ggctgcacac gctcccaacc   1500
tggattgcca gcgacagcgc tgaagcggtg catattgccg aacagatagg ctatccggta   1560
gctctcaagc tgcgctcgcc cgacattccg cataaatctg aagttcaggg ggtcatgctt   1620
tacctgcgga ccgcaagcga ggtacaacag gccgcgaacg ctattttga tcgtgtaaag   1680 atggcctggc cgcaagcgcg gattcacggt ttgctggtac aaagcatggc taaccgcgcc   1740
ggcgcgcagg agcttcgtgt ggtggtcgag cacgatccgg tgtttggtcc tttgattatg   1800
ttgggtgaag gcggcgtaga gtggcgtccg gaagagcagg ctgtcgtcgc gctgccgccg   1860
ctcaacatga acctgcgcg ctatctggtg attcagggca ttaaacagcg gaaaattcgc   1920
gcccgtagcg cgctgcgtcc gctggatatt gtcggtttaa gccaattgct ggtccaggtt   1980
tcaaacctga ttgtcgactg cccggaaatt cagcgtctgg atatccatcc gctgctggct   2040
tccgccagtg agtttaccgc gctggatgtg acgctggata ttgccccgtt tgatggcgat   2100
aacgaaagtc gacttgcggt acgcccctat ccccaccagc ttgaagagtg ggtggagatg   2160
aaaaatggcg atcgctgcct gttccgtcct atcctgccgg aagatgagcc caactgcga   2220 caattcatcg cacaggtcac caaagaggat ctttactacc gttatttcag cgagatcaac   2280
gaattcaccc atgaagattt agccaacatg acgcagatcg actacgatcg agaaatggcc   2340
tttgtggccg tgaggcggat ggacaatgct gaagagatcc tcggcgtaac gcgcgcgatc   2400
tccgatcctg acaacgtaga tgccgaattt gccgtattgg tgcgttcaga tctcaaaggg   2460
ttgggtttag gacgccgttt aatggagaaa ttgattgcct atactcgcga tcacggattg   2520
aagcggctga acgtattac gatgccaaac aatcgcggca tggtcgcgct ggccagaaaa   2580
ctgggatttc aggtcgatat tcagctcgaa gagggcatcg tgggattgac gctgaatctg   2640
gccaaatgtg atgaatcgtg a                                            2661
```

<210> SEQ ID NO 2
<211> LENGTH: 7
<212> TYPE: PRT
<213> ORGANISM: Artificial Sequence
<220> FEATURE:
<223> OTHER INFORMATION: Artificial: short polypeptide
<220> FEATURE:
<221> NAME/KEY: MISC_FEATURE
<222> LOCATION: (2)..(5)
<223> OTHER INFORMATION: Can be any amino acid

<400> SEQUENCE: 2

Pro Xaa Xaa Xaa Xaa Gly Lys
1               5

<210> SEQ ID NO 3
<211> LENGTH: 27
<212> TYPE: DNA
<213> ORGANISM: Artificial Sequence

```
<220> FEATURE:
<223> OTHER INFORMATION: Artificial: PCR primer

<400> SEQUENCE: 3
gagaacaacc atatgagcca aacacat                                    27

<210> SEQ ID NO 4
<211> LENGTH: 35
<212> TYPE: DNA
<213> ORGANISM: Artificial Sequence
<220> FEATURE:
<223> OTHER INFORMATION: Artificial: PCR primer

<400> SEQUENCE: 4 aacccgctc ttccgcatga cggcatcgcg atggc                            35

<210> SEQ ID NO 5
<211> LENGTH: 6
<212> TYPE: PRT
<213> ORGANISM: Artificial Sequence
<220> FEATURE:
<223> OTHER INFORMATION: Artificial: Short polypeptide

<400> SEQUENCE: 5

Ser Gly Lys Ile Met Arg
1               5

<210> SEQ ID NO 6
<211> LENGTH: 4
<212> TYPE: PRT
<213> ORGANISM: Artificial Sequence
<220> FEATURE:
<223> OTHER INFORMATION: Artificial: Short polypeptide

<400> SEQUENCE: 6

Ser Gly Lys Ile
1

<210> SEQ ID NO 7
<211> LENGTH: 5
<212> TYPE: PRT
<213> ORGANISM: Artificial Sequence
<220> FEATURE:
<223> OTHER INFORMATION: Artificial: Short polypeptide

<400> SEQUENCE: 7

Ser Gly Lys Ile Met
1               5

<210> SEQ ID NO 8
<211> LENGTH: 5
<212> TYPE: PRT
<213> ORGANISM: Artificial Sequence
<220> FEATURE:
<223> OTHER INFORMATION: Artificial: Short polypeptide

<400> SEQUENCE: 8

Gly Lys Ile Met Arg
1               5

<210> SEQ ID NO 9
<211> LENGTH: 4
<212> TYPE: PRT
<213> ORGANISM: Artificial Sequence
<220> FEATURE:
<223> OTHER INFORMATION: Artificial: Short polypeptide
```

<400> SEQUENCE: 9

Lys Ile Met Arg
1

<210> SEQ ID NO 10
<211> LENGTH: 244
<212> TYPE: DNA
<213> ORGANISM: Salmonella enterica
<220> FEATURE:
<221> NAME/KEY: misc_feature
<222> LOCATION: (16)..(16)
<223> OTHER INFORMATION: Can be any nucleotide
<220> FEATURE:
<221> NAME/KEY: misc_feature
<222> LOCATION: (28)..(29)
<223> OTHER INFORMATION: Can be any nucleotide
<220> FEATURE:
<221> NAME/KEY: misc_feature
<222> LOCATION: (33)..(33)
<223> OTHER INFORMATION: Can be any nucleotide
<220> FEATURE:
<221> NAME/KEY: misc_feature
<222> LOCATION: (36)..(36)
<223> OTHER INFORMATION: Can be any nucleotide
<220> FEATURE:
<221> NAME/KEY: misc_feature
<222> LOCATION: (39)..(39)
<223> OTHER INFORMATION: Can be any nucleotide
<220> FEATURE:
<221> NAME/KEY: misc_feature
<222> LOCATION: (44)..(46)
<223> OTHER INFORMATION: Can be any nucleotide
<220> FEATURE:
<221> NAME/KEY: misc_feature
<222> LOCATION: (50)..(50)
<223> OTHER INFORMATION: Can be any nucleotide
<220> FEATURE:
<221> NAME/KEY: misc_feature
<222> LOCATION: (55)..(55)
<223> OTHER INFORMATION: Can be any nucleotide
<220> FEATURE:
<221> NAME/KEY: misc_feature
<222> LOCATION: (63)..(63)
<223> OTHER INFORMATION: Can be any nucleotide
<220> FEATURE:
<221> NAME/KEY: misc_feature
<222> LOCATION: (68)..(68)
<223> OTHER INFORMATION: Can be any nucleotide
<220> FEATURE:
<221> NAME/KEY: misc_feature
<222> LOCATION: (204)..(204)
<223> OTHER INFORMATION: Can be any nucleotide
<220> FEATURE:
<221> NAME/KEY: misc_feature
<222> LOCATION: (227)..(227)
<223> OTHER INFORMATION: Can be any nucleotide
<220> FEATURE:
<221> NAME/KEY: misc_feature
<222> LOCATION: (229)..(229)
<223> OTHER INFORMATION: Can be any nucleotide
<220> FEATURE:
<221> NAME/KEY: misc_feature
<222> LOCATION: (231)..(231)
<223> OTHER INFORMATION: Can be any nucleotide
<220> FEATURE:
<221> NAME/KEY: misc_feature
<222> LOCATION: (233)..(233)
<223> OTHER INFORMATION: Can be any nucleotide

<400> SEQUENCE: 10
agccaccttt ttgggnaacc ggcggggnnt tanggncana caannngggn tttgnaccag    60
caaaccgnga atccgcgctt gcggccaggc catctttaca cgatcaaaaa tagcgttcgc   120
ggcctgttgt acctcgcttg cggtccgcag gtaaagcatg accccctgaa cttcagattt   180

```
atgcggaatg tcgggcgagc gcanccttga gagctaccgg atagccnanc ngnttttttt    240
tttt                                                                 244
```

<210> SEQ ID NO 11
<211> LENGTH: 150
<212> TYPE: DNA
<213> ORGANISM: Salmonella enterica
<220> FEATURE:
<221> NAME/KEY: misc_feature
<222> LOCATION: (8)..(8)
<223> OTHER INFORMATION: Can be any nucleotide
<220> FEATURE:
<221> NAME/KEY: misc_feature
<222> LOCATION: (10)..(10)
<223> OTHER INFORMATION: Can be any nucleotide
<220> FEATURE:
<221> NAME/KEY: misc_feature
<222> LOCATION: (12)..(12)
<223> OTHER INFORMATION: Can be any nucleotide
<220> FEATURE:
<221> NAME/KEY: misc_feature
<222> LOCATION: (22)..(23)
<223> OTHER INFORMATION: Can be any nucleotide
<220> FEATURE:
<221> NAME/KEY: misc_feature
<222> LOCATION: (25)..(25)
<223> OTHER INFORMATION: Can be any nucleotide
<220> FEATURE:
<221> NAME/KEY: misc_feature
<222> LOCATION: (29)..(29)
<223> OTHER INFORMATION: Can be any nucleotide
<220> FEATURE:
<221> NAME/KEY: misc_feature
<222> LOCATION: (38)..(38)
<223> OTHER INFORMATION: Can be any nucleotide
<220> FEATURE:
<221> NAME/KEY: misc_feature
<222> LOCATION: (42)..(42)
<223> OTHER INFORMATION: Can be any nucleotide
<220> FEATURE:
<221> NAME/KEY: misc_feature
<222> LOCATION: (55)..(55)
<223> OTHER INFORMATION: Can be any nucleotide
<220> FEATURE:
<221> NAME/KEY: misc_feature
<222> LOCATION: (57)..(57)
<223> OTHER INFORMATION: Can be any nucleotide
<220> FEATURE:
<221> NAME/KEY: misc_feature
<222> LOCATION: (71)..(71)
<223> OTHER INFORMATION: Can be any nucleotide
<220> FEATURE:
<221> NAME/KEY: misc_feature
<222> LOCATION: (73)..(73)
<223> OTHER INFORMATION: Can be any nucleotide
<220> FEATURE:
<221> NAME/KEY: misc_feature
<222> LOCATION: (91)..(91)
<223> OTHER INFORMATION: Can be any nucleotide
<220> FEATURE:
<221> NAME/KEY: misc_feature
<222> LOCATION: (106)..(106)
<223> OTHER INFORMATION: Can be any nucleotide
<220> FEATURE:
<221> NAME/KEY: misc_feature
<222> LOCATION: (108)..(108)
<223> OTHER INFORMATION: Can be any nucleotide
<220> FEATURE:
<221> NAME/KEY: misc_feature
<222> LOCATION: (114)..(114)
<223> OTHER INFORMATION: Can be any nucleotide
<220> FEATURE:
<221> NAME/KEY: misc_feature
<222> LOCATION: (117)..(117)
<223> OTHER INFORMATION: Can be any nucleotide
<220> FEATURE:
<221> NAME/KEY: misc_feature

```
<222> LOCATION: (122)..(123)
<223> OTHER INFORMATION: Can be any nucleotide
<220> FEATURE:
<221> NAME/KEY: misc_feature
<222> LOCATION: (125)..(125)
<223> OTHER INFORMATION: Can be any nucleotide
<220> FEATURE:
<221> NAME/KEY: misc_feature
<222> LOCATION: (132)..(132)
<223> OTHER INFORMATION: Can be any nucleotide
<220> FEATURE:
<221> NAME/KEY: misc_feature
<222> LOCATION: (136)..(137)
<223> OTHER INFORMATION: Can be any nucleotide
<220> FEATURE:
<221> NAME/KEY: misc_feature
<222> LOCATION: (139)..(139)
<223> OTHER INFORMATION: Can be any nucleotide
<220> FEATURE:
<221> NAME/KEY: misc_feature
<222> LOCATION: (141)..(142)
<223> OTHER INFORMATION: Can be any nucleotide
<220> FEATURE:
<221> NAME/KEY: misc_feature
<222> LOCATION: (147)..(148)
<223> OTHER INFORMATION: Can be any nucleotide

<400> SEQUENCE: 11
agcttttngn tnccgacagg tnngnggcng cgtcatcntg tnaatgccat ggacnanatg     60
cgtaggcgcg nangagcttc gtgtggtggt ngatcactat ccagtnctg atgnttntcc    120 tnnanatgat gngaanncnc nnacaanntt                                    150

<210> SEQ ID NO 12
<211> LENGTH: 13
<212> TYPE: PRT
<213> ORGANISM: Salmonella enterica

<400> SEQUENCE: 12

Asp Ser Leu Pro Lys Thr Arg Ser Gly Lys Ile Met Arg
1               5                   10

<210> SEQ ID NO 13
<211> LENGTH: 13
<212> TYPE: PRT
<213> ORGANISM: Salmonella enterica

<400> SEQUENCE: 13

Ser Gln Leu Pro Lys Thr Arg Ser Gly Lys Met Leu Arg
1               5                   10

<210> SEQ ID NO 14
<211> LENGTH: 13
<212> TYPE: PRT
<213> ORGANISM: Saccharomyces cerevisiae

<400> SEQUENCE: 14

Arg Asp Leu Pro Arg Thr Arg Ser Gly Lys Ile Met Arg
1               5                   10

<210> SEQ ID NO 15
<211> LENGTH: 13
<212> TYPE: PRT
<213> ORGANISM: Photinus pyralis

<400> SEQUENCE: 15

Asp Glu Val Pro Lys Gly Leu Thr Gly Lys Leu Asp Ala
1               5                   10
```

<210> SEQ ID NO 16
<211> LENGTH: 13
<212> TYPE: PRT
<213> ORGANISM: Brevibacillus brevis

<400> SEQUENCE: 16

Asp Lys Met Pro Leu Thr Ser Asn Gly Lys Ile Asp Arg
1               5                   10

<210> SEQ ID NO 17
<211> LENGTH: 13
<212> TYPE: PRT
<213> ORGANISM: Amycolatopsis orientalis

<400> SEQUENCE: 17

Asp Ala Leu Pro Leu Thr Ala Asn Gly Lys Val Asp Arg
1               5                   10

<210> SEQ ID NO 18
<211> LENGTH: 13
<212> TYPE: PRT
<213> ORGANISM: Amycolatopsis orientalis

<400> SEQUENCE: 18

Asp Ala Leu Pro Leu Thr Ala His Gly Lys Ile Asp Arg
1               5                   10

<210> SEQ ID NO 19
<211> LENGTH: 13
<212> TYPE: PRT
<213> ORGANISM: Amycolatopsis orientalis

<400> SEQUENCE: 19

Asp Ala Leu Pro Leu Thr Thr Asn Gly Lys Val Asp Arg
1               5                   10

<210> SEQ ID NO 20
<211> LENGTH: 13
<212> TYPE: PRT
<213> ORGANISM: Streptomyces coelicolor

<400> SEQUENCE: 20

Pro Arg Leu Pro Val Thr Pro Asn Gly Lys Leu Asp Arg
1               5                   10

<210> SEQ ID NO 21
<211> LENGTH: 13
<212> TYPE: PRT
<213> ORGANISM: Streptomyces coelicolor

<400> SEQUENCE: 21

Asp Val Leu Pro Leu Thr Pro Asn Gly Lys Leu Asp Thr
1               5                   10

<210> SEQ ID NO 22
<211> LENGTH: 13
<212> TYPE: PRT
<213> ORGANISM: Streptomyces coelicolor

<400> SEQUENCE: 22

Asp Ala Leu Pro Leu Thr Leu Asn Gly Lys Leu Asp Arg
1               5                   10

<210> SEQ ID NO 23

```
<211> LENGTH: 13
<212> TYPE: PRT
<213> ORGANISM: Streptomyces coelicolor

<400> SEQUENCE: 23

Asp Ala Leu Pro Leu Thr Pro Asn Gly Lys Leu Asp Arg
1               5                   10

<210> SEQ ID NO 24
<211> LENGTH: 652
<212> TYPE: PRT
<213> ORGANISM: Salmonella enterica

<400> SEQUENCE: 24

Met Ser Gln Thr His Lys His Ala Ile Pro Ala Asn Ile Ala Asp Arg
1               5                   10                  15

Cys Leu Ile Asn Pro Glu Gln Tyr Glu Thr Lys Tyr Lys Gln Ser Ile
                20                  25                  30

Asn Asp Pro Asp Thr Phe Trp Gly Glu Gln Gly Lys Ile Leu Asp Trp
            35                  40                  45

Ile Thr Pro Tyr Gln Lys Val Lys Asn Thr Ser Phe Ala Pro Gly Asn
        50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
                85                  90                  95

Trp Glu Gly Asp Asp Thr Ser Gln Ser Lys His Ile Ser Tyr Arg Glu
            100                 105                 110

Leu His Arg Asp Val Cys Arg Phe Ala Asn Thr Leu Leu Asp Leu Gly
        115                 120                 125

Ile Lys Lys Gly Asp Val Val Ala Ile Tyr Met Pro Met Val Pro Glu
    130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Ser Ser Arg Leu Val Ile Thr Ala Asp Glu Gly Val Arg Ala
            180                 185                 190

Gly Arg Ser Ile Pro Leu Lys Lys Asn Val Asp Asp Ala Leu Lys Asn
        195                 200                 205

Pro Asn Val Thr Ser Val Glu His Val Ile Val Leu Lys Arg Thr Gly
    210                 215                 220

Ser Asp Ile Asp Trp Gln Glu Gly Arg Asp Leu Trp Trp Arg Asp Leu
225                 230                 235                 240

Ile Glu Lys Ala Ser Pro Glu His Gln Pro Glu Ala Met Asn Ala Glu
                245                 250                 255

Asp Pro Leu Phe Ile Leu Tyr Thr Ser Gly Ser Thr Gly Lys Pro Lys
            260                 265                 270

Gly Val Leu His Thr Thr Gly Gly Tyr Leu Val Tyr Ala Ala Thr Thr
        275                 280                 285

Phe Lys Tyr Val Phe Asp Tyr His Pro Gly Asp Ile Tyr Trp Cys Thr
    290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
                325                 330                 335
```

-continued

```
Pro Thr Pro Ala Arg Met Cys Gln Val Val Asp Lys His Gln Val Asn
            340             345             350

Ile Leu Tyr Thr Ala Pro Thr Ala Ile Arg Ala Leu Met Ala Glu Gly
            355             360             365

Asp Lys Ala Ile Glu Gly Thr Asp Arg Ser Ser Leu Arg Ile Leu Gly
    370             375             380

Ser Val Gly Glu Pro Ile Asn Pro Glu Ala Trp Glu Trp Tyr Trp Lys
385             390             395             400

Lys Ile Gly Lys Glu Lys Cys Pro Val Val Asp Thr Trp Trp Gln Thr
            405             410             415

Glu Thr Gly Gly Phe Met Ile Thr Pro Leu Pro Gly Ala Ile Glu Leu
            420             425             430

Lys Ala Gly Ser Ala Thr Arg Pro Phe Phe Gly Val Gln Pro Ala Leu
            435             440             445

Val Asp Asn Glu Gly His Pro Gln Glu Gly Ala Thr Glu Gly Asn Leu
    450             455             460

Val Ile Thr Asp Ser Trp Pro Gly Gln Ala Arg Thr Leu Phe Gly Asp
465             470             475             480

His Glu Arg Phe Glu Gln Thr Tyr Phe Ser Thr Phe Lys Asn Met Tyr
            485             490             495

Phe Ser Gly Asp Gly Ala Arg Arg Asp Glu Asp Gly Tyr Tyr Trp Ile
            500             505             510

Thr Gly Arg Val Asp Asp Val Leu Asn Val Ser Gly His Arg Leu Gly
            515             520             525

Thr Ala Glu Ile Glu Ser Ala Leu Val Ala His Pro Lys Ile Ala Glu
    530             535             540

Ala Ala Val Val Gly Ile Pro His Ala Ile Lys Gly Gln Ala Ile Tyr
545             550             555             560

Ala Tyr Val Thr Leu Asn His Gly Glu Glu Pro Ser Pro Glu Leu Tyr
            565             570             575

Ala Glu Val Arg Asn Trp Val Arg Lys Glu Ile Gly Pro Leu Ala Thr
            580             585             590

Pro Asp Val Leu His Trp Thr Asp Ser Leu Pro Lys Thr Arg Ser Gly
    595             600             605

Lys Ile Met Arg Arg Ile Leu Arg Lys Ile Ala Ala Gly Asp Thr Ser
    610             615             620

Asn Leu Gly Asp Thr Ser Thr Leu Ala Asp Pro Gly Val Val Glu Lys
625             630             635             640

Leu Leu Glu Glu Lys Gln Ala Ile Ala Met Pro Ser
            645             650
```

METHOD OF CONTROLLING ACETYLATION OF METABOLIC ENZYMES

CROSS-REFERENCE TO RELATED APPLICATIONS

This application claims the benefit of U.S. Provisional Application No. 60/387,557 filed Jun. 7, 2002.

STATEMENT REGARDING FEDERALLY SPONSORED RESEARCH OR DEVELOPMENT

This invention was made with United States government support awarded by the following agency: NIH, Grant Number GM62203. The United States has certain rights in this invention.

BACKGROUND OF THE INVENTION

Short-chain fatty acids (SCFAs) such as acetate and propionate are used as sources of carbon and energy by prokaryotes occupying diverse habitats such as soil, where acetate and propionate are the most abundant fatty acids, or the gastrointestinal tract of humans where the concentration of acetate and propionate can reach high levels. All catabolic pathways for acetate and propionate require these SCFAs to be activated into their corresponding SCFAcyl-CoA forms before they can be converted into metabolites that can enter central metabolism. Acetyl-CoA feeds directly into the TCA cycle, whereas propionyl-CoA can be catabolized via a number of different pathways that convert it into pyruvate, acetate or succinyl-CoA, which then enter the TCA cycle. Thus the regulation of the enzymes which control the conversion of acetate to acetyl-CoA and propionate to propionyl-CoA regulates the entry, in turn, of these basic feedstock molecules into the metabolic systems of many organisms. For example, acetyl CoA and propionyl-CoA are essential precursors of antibiotic production in some organisms.

In enteric bacteria such as *Escherichia coli* and *Salmonella enterica*, acetate is enzymatically converted into acetyl-CoA via either one of two pathways. The first pathway requires the involvement of the acetate kinase (AckA, EC 2.7.2.1) and phosphotransacetylase (Pta, EC 2.3.1.8) enzymes. In these bacteria, the enzymes AckA and Pta are responsible for the synthesis of acetyl-CoA when acetate is present in high concentrations in the environment ($\geq 30$ mM acetate). This pathway is considered to be the low-affinity pathway for acetate activation. The second pathway for the activation of acetate requires the activity of the enzyme known as ATP-dependent acetate:CoA ligase (AMP forming; EC 6.2.1.1; aka acetyl-CoA synthetase) encoded by the acs gene. Acs is required when the concentration of acetate in the environment is low ($\leq 10$ mM acetate), and thus this pathway is considered to be the high-affinity, or principle, pathway for acetate activation in the bacteria. In *S. enterica* propionate can be converted enzymatically to propionyl-CoA by the ATP-dependent propionate:CoA ligase (AMP forming, EC 6.2.1.17; aka propionyl-CoA synthetase) encoded by the prpE gene, which is a part of the prpBCDE operon. The prpBCDE operon of this bacterium encodes several of the functions needed for the catabolism of propionate. In addition, *S. enterica* has two distinct propionate kinases (PduW, TdcD), but the genes encoding these enzymes (pduW, tdcD) are part of the propanediol utilization (pduABCDEGHJKLMNOPQSTUVWX) and threonine decarboxylation (tdcBCDEG) operons whose expression is induced only under specific growth conditions. Hence, under conditions where the pduW and tdcD genes are not expressed, propionate activation to propionyl-CoA occurs only via the high-affinity propionyl-CoA synthetase-dependent pathway based on the enzyme encoded by the prpE gene.

There is significant interest in understanding the functioning of these enzymes and understanding how the activity of the enzymes can be regulated. The use of bacteria to produce biomolecules of interest requires that the feedstock molecules be produced in abundance. Yet the mechanisms which control the regulation of these enzymes in their native hosts are obscure. Currently, it is not known how the enzymatic activities of acetyl-CoA synthetase and propionyl-CoA synthetase are regulated. Understanding how the activity of these enzymes are regulated permits the intelligent design of modified bacteria which can accumulate feedstocks for useful reactions and metabolite accumulation in a manner not possible before.

SUMMARY OF THE INVENTION

In one aspect, the present invention relates to a method of modulating the activity of an AMP-forming enzyme (AFE) by modulating acetylation of the enzyme at a lysine residue. An AFE is active when nonacetylated or de-acetylated and inactive when acetylated.

In another aspect, the present invention relates to an isolated nucleic acid that contains a nucleotide sequence encoding the protein product of the yfiQ gene or one of its homologues and a non-native promoter operably linked to the nucleotide sequence. The protein product of the yfiQ gene or its homologues can acetylize AFEs. A host cell that contains the nucleic acid described above is also within the scope of the present invention. The present invention also encompasses an antibody against the protein product of the yfiQ gene or one of its homologues.

In another aspect, the present invention relates to an isolated polypeptide that contains the amino acid sequence of an acetyl-CoA synthetase with the amino acid that is either leucine 641 of the acs gene product or its equivalent substituted by another amino acid (e.g., proline). An antibody against the acetyl-CoA synthetase with the substitution is also with the scope of the present invention.

In another aspect, the present invention relates to an isolated nucleic acid that contains a nucleotide sequence encoding the acetyl-CoA synthetase with the substitution described above. The isolated nucleic acid can be a vector that further contains a non-native promoter to which the coding sequence is operably linked. The present invention also encompasses a host cell that contains the vector.

Other aspects of the present invention relate to methods of modulating cellular acetyl-CoA or propionyl-CoA levels, methods of identifying agents that can modulate the activity of AFE acetylases, and methods of identifying AFE mutants that are insensitive to acetylation regulation.

BRIEF DESCRIPTION OF THE DRAWINGS

FIG. 1A illustrates synthesis of acetyl-CoA by Acs.

FIG. 1B demonstrates the presence of acetylated residues in inactive Acs by immunoblotting using polyclonal anti-N-acetyl-lysine antibody. cobB$^+$, cobB$^-$ indicate the genotype of the strain from which Acs was isolated. Acs from cobB$^-$ cells was incubated with purified CobB as described in the Examples for the periods of time indicated.

FIG. 3 shows conserved motif containing the acetylation site lysine residue amongst representative members of the AMP-forming family of proteins. Acs, acetylCoA synthetase (gi:16767525, *S. enterica*, protein amino acid sequence defined by SEQ ID NO:24); PrpE, propionyl-CoA synthetase (gi:14917034, *S. enterica*); Acs2p, acetyl-CoA synthetase (gi:6323182, *S. cerevisiae*); GrsA, gramicidin S synthetase I (gi:3334467, *B. brevis*), CepA, one of three subunits that synthesize chloroeremomycin (EMBL accession numbers X98690, S46968; gi :7522085, *Amycolotopsis orientalis*); cda PSI, calcium-dependent antibiotic peptide synthetase I (ORF SCO3230, *S. coelicolor*). The motif PX4GK was used to identify putative substrates of sirtuins.

FIG. 4 shows yfiQ coding sequence (highlighted segments correspond to matched regions from sequence analysis).

DETAILED DESCRIPTION OF THE INVENTION

Figure 1:
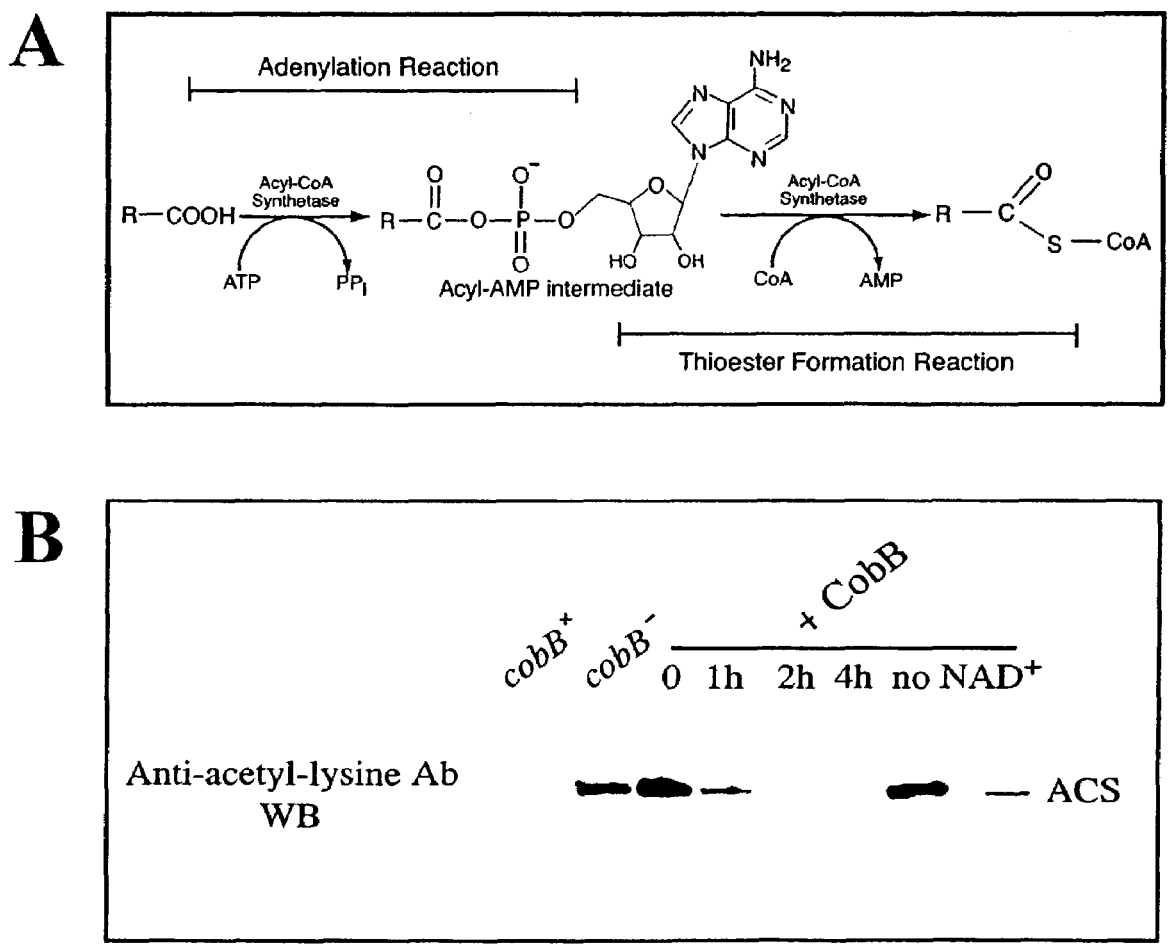
In FIG. 1, R indicates the structure of the acid including $C_\alpha$.
Figure 2:
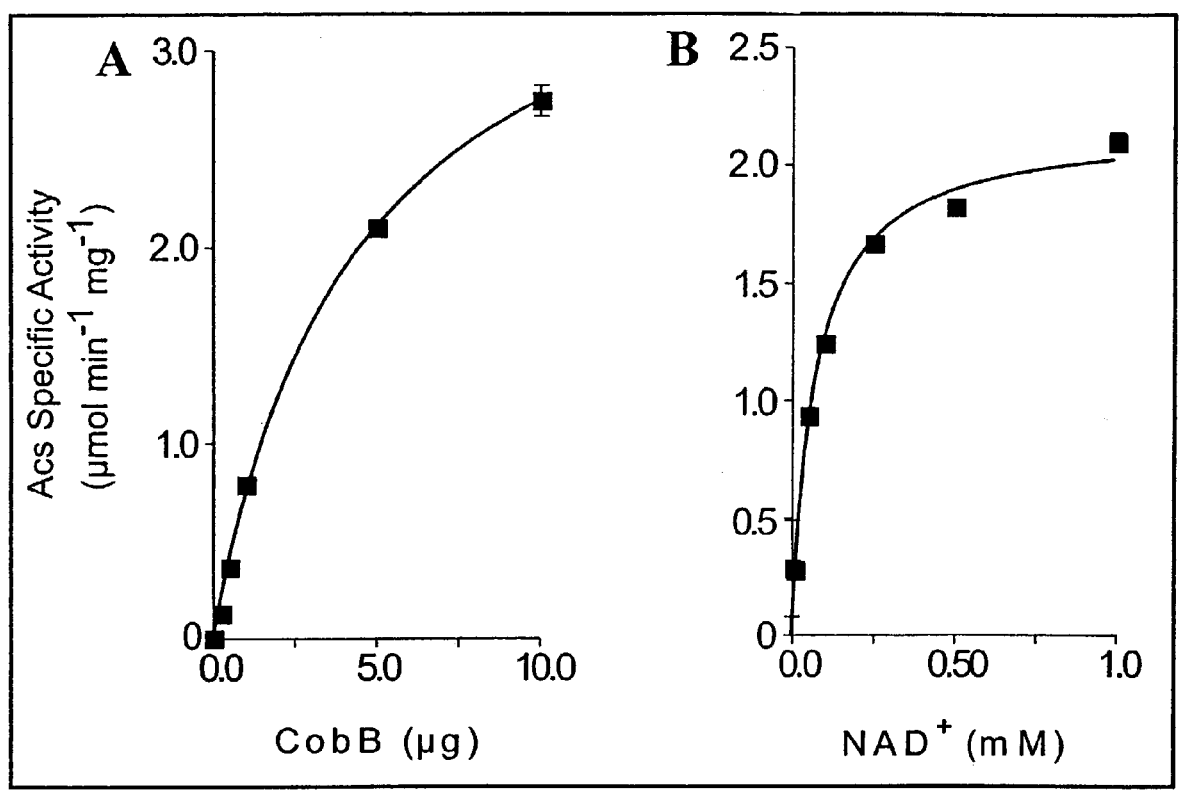
FIG. 2 is a graphical illustration of data showing CobB-dependent (A) and NAD$^+$-dependent (B) Acs activation.

It has been discovered and reported here that the activity of the enzymes acetyl-CoA synthetase (Acs) and propionyl-CoA synthetase (PrpE) is regulated in their native hosts by a process of acetylation and de-acetylation. The enzymes are inactive when acetylated and active when de-acetylated. The state of activation of these enzymes is, in turn, controlled by other enzymes, which are identified here. Understanding the mechanism this acetylation process also permits the process to be controlled or disrupted, as desired, in specific microbial hosts. For example, the acetylation is characterized by the attachment of the acetyl group to a specific lysine residue in each enzyme. By making modified forms of the enzymes in which it is not possible to attach an acetyl group to that specific lysine residue, it becomes possible to make enzymes which are always active. Using this approach, a bacterial host can be made to produce the modified form of the enzymes, and the bacterial host will accumulate acetyl-CoA and propionate-CoA to levels not achieved by bacteria with only native forms of these enzymes.

The investigation that lead to this insight began with discovering that a class of protein known as a sirtuin functions to control the activity of the Acs and PrpE enzymes. A sirtuin known as SIR2 was previously known to have NAD+-dependent histone de-actylase activity. Here it was found that the SIR2 enzyme acts to de-acetylate, and thereby activate, the Acs enzyme. The function of sirtuins is conserved across living organisms to the extent that a human sirtuin will restore the functioning of a bacteria deficient in the bacterial sirtuin CobB. This knowledge provides methodology to alter the activity of Acs and PrpE in bacterial hosts. By increasing the activity of the sirtuins responsible for the de-acetylation activity, it is possible to increase the activity of the Acs or PrpE enzymes. Alternatively, by preventing the acetylation of the enzymes, increased enzyme activity can be achieved.

Thus, specifically, the inventors here have found that acetylation and de-acetylation of the acetyl-CoA synthetase, or Acs, enzyme at the lysine residue 609 regulates the activity of the enzyme. The non-acetylated or de-acetylated form of the enzyme is the active form and the acetylated form is the inactive form. When a single point mutation is created in the acetyl-CoA synthetase, a change of a leucine at residue 641 to a proline (L641P), the proline acts to block access to the lysine at residue 609. This modified form of the synthetase, designed L641P, is resistant to acetylation inactivation at lysine 609. This result demonstrates that enzymes which share this common, and highly conserved, lysine residue can be altered to avoid acetylation and deactivation.

The inventors have also identified one gene for an enzyme that is responsible for acetylating the acetyl-CoA synthetase in bacteria. The protein YifQ, which is encoded by the yifQ gene, acetylates, and thus inactivates the acetyl-CoA synthetase. It has also been discovered that he protein product of the cobB gene deacetylates, and thus reactivates, the acetyl-CoA synthetase. Further, the inventors have discovered that acetylation of the acetyl-CoA synthetase at lysine 609 blocks the adenylate intermediate-forming (AMP-forming) activity but not the thioester-forming activity of the enzyme. Other AMP-forming enzymes (AFEs), in particular enzymes of the non-ribosomal peptide synthetase enzymes (NRPS), also have lysines in positions that correspond to lysine 609 of acetyl-CoA synthetase and these lysine residues have been shown to be important for the activity of the enzymes. It is expected that as a general rule AFEs and NRPS are regulated by acetylation and deacetylation at a lysine that corresponds to lysine 609 of the acetyl-CoA synthetase. In addition, AFEs (e.g., acetyl-CoA synthetase and propionyl-CoA synthetase), members of the SIR2 protein family to which CobB belongs (i.e., CobB and homologues) and members of the protein family to which YfiQ belongs (i.e., YfiQ and homologues) are highly conserved among all prokaryotic and eukaryotic species. It is expected that the activity of an AFE in a particular species is regulated through acetylation and deacetylation by the YfiQ and CobB homologues in that species. Furthermore, it is expected that YfiQ and CobB homologues from different species can replace each other for acetylation and deacetylation of AFEs. For example, the inventors have found that yeast and human SIR2 proteins can replace bacterial CobBs for deacetylating bacterial acetyl-CoA synthetase.

It is also possible to raise antibodies that are specific to the lysine-containing region of these enzymes. For example, the Acs enzyme can be cleaved into peptides and the peptide containing the lysine at residue 609 can be used to raise antibodies to that location of the protein. Then those antibodies can be used to probe other protein enzymes sharing this feature. The other proteins thus identified will also be substrates for YifQ and CobB enzymes, to inhibit or activate the activity of the enzymes thus identified.

The identification of the gene responsible for the enzyme which acetylates Acs, yfiQ, makes possible the expression, suppression or modification of the gene and its enzyme YifQ. Thus, the present invention relates to an isolated polypeptide that contains the protein product of the yfiQ gene or its homologues.

Again, it is specifically envisioned that modified form of enzymes can be designed to take advantage of the insights described here. It now becomes possible to design enzymes, such as the L641P enzyme, which are resistant to the intracellular processes which would otherwise tend to control the activity level of the enzyme. This makes it possible to design bacterial hosts which will accumulate enzymatic products, such as acetyl-CoA, in concentrations that would not be achieved in non-engineered forms of the bacteria.

In another aspect, the present invention relates to a method of modulating the activity of an AFE or an NRPS by modulating acetylation of the enzyme. These methods would be useful for any enzyme in this class for which the non-acetylated or deacetylated state of the enzyme is the active state and acetylated state is the inactive state. Examples of AFEs whose activities can be modulated by the method include but are not limited to non-ribosomal peptide synthetases, acetyl-CoA synthetase, propionyl-CoA synthetase, luciferase, aryl-CoA synthetases and acyl-CoA synthetases.

In one embodiment, acetylation of the enzyme is modulated by changing the activity of an AFE acetylase, an AFE deacetylase, or both. In the absence of any functional AFE acetylase, or when at least one AFE acetylase and at least one AFE deacetylase are present and the activity of the AFE acetylase is relatively low in comparison to that of the AFE deacetylase, the AFE will be mainly in its non-acetylated (active) state. In the absence of any functional AFE-deacetylase and the presence of at least one AFE acetylase, or when at least one AFE acetylase and at least one AFE deacetylase are present and the activity of the AFE deacetylase is relatively low in comparison to that of the AFE acetylase, the AFE will be mainly in the acetylated (inactive) state. There are many ways that one can change the activity of an AFE acetylase or deacetylase. A skilled artisan is familiar with these ways. For example, extraneous yfiQ gene, cobB gene or both can be introduced into a cell and their expression can be regulated by using suitable promoters. Antibodies and antisense techniques can be used to block the activity of an AFE acetylase or deacetylase. Agents that can modulate the activity of AFE acetylase or deacetylase can also be used. A screening method for identifying such agents is described below.

The method of modulating the activity of an AFE may also find utility in treating clinical conditions and diseases that are related to an abnormal level of an AFE activity. Further, some human pathogens such as *Salmonella* and enteropathogenic *E. coli* O157:H7 may rely on the high levels of short chain fatty acids in the intestine for catabolism. Short chain fatty acids are products of the AFE acyl-CoA synthetases. Thus, the method may also be used to weaken or kill the pathogens by inhibiting the activity of the acyl-CoA synthetases. In addition, *E. coli* has been used to produce certain antimicrobial (e.g., polyketides) and anti-cancer agents. Propionyl-CoA and acetyl-CoA are precursors for these agents. Acyl-CoA synthetases such as PrpE have been genetically engineered into *E. coli* for the purpose of increasing the availability of propionyl-CoA and acetyl-CoA for the synthesis of the agents. The problem with the approach is that although the enzymes are expressed, some of them are inactive. It is expected that inhibiting the activity of YfiQ and/or increasing the activity of CobB in *E. coli* will overcome the problem. It is also expected that the introduction of an appropriate CobB protein or its homolog into *E. coli* will solve the problem of inactive heterologous, recombinant enzymes.

In another aspect, the present invention relates to a method of modulating the acetyl-CoA or propionyl-CoA level in a cell by modulating the activity of an AFE acetylase in the cell. An increase in acetylase activity will lead to a decrease in the level of acetyl-CoA or propionyl-CoA and a decrease in acetylase activity will lead to an increase in the level of acetyl-CoA or propionyl-CoA. In addition, the method may optionally involve modulating the activity of an AFE deacetylase as well. There are many ways one can regulate the cellular activity of an AFE acetylase or deacetylase and a skilled artisan is familiar with them. Examples have been provided above in connection with the method of modulating the activity of AFEs.

In another aspect, the present invention relates to a method of identifying an agent that can modulate the activity of an AFE acetylase. The method involves providing a composition that contains the AFE acetylase and an AFE, exposing the composition to a test agent under the conditions which allow the acetylase to acetylate and thus inactivate the AFE, determining the AFE acetylation status, and comparing the acetylation status of the AFE to that of AFE from a control composition that is not exposed to the test agent. If more AFE in the treated composition is acetylated than the control composition, the test agent is then identified as being able to enhance the activity of the AFE acetylase. If less AFE in the treated composition is acetylated than the control composition, the test agent is subsequently identified as being able to decrease the activity of the AFE acetylase. The assay system described above can be an in vivo or an in vitro system and detailed experimental conditions can be readily determined by a skilled artisan. For example, a cobB-negative and yfiQ-positive bacterial cell can be used to screen for agents that can modulate the activity of the yfiQ protein. Any AFE can be used in this method. Preferred AFEs for the method are those whose acetylation sites (lysine(s)) are known. Examples of such AFEs include but are not limited to acetyl-CoA synthetase, propionyl-CoA synthetase, luciferase and gramicidin synthetase 1.

Alternatively in the above method, the enzymatic activity of the AFE rather than acetylation status is used as the end point for screening. A skilled artisan knows how to measure the activity of an AFE. For example, a substrate of the AFE can be included in the assay system so that the AFE activity can be determined by measuring the amount of product at the end of the assay. In this alternative, when the AFE activity is found to be changed, further experiments should be conducted to determine whether the test agent modulated the AFE activity directly or through the AFE acetylase. Note in particular the comparative sequence data presented in FIG. 3 which illustrates the protein sequence motif of PXXXXGK (SEQ ID NO:2) which is characteristic of enzymes which have a lysine that is subject to acetylation as described here.

In another aspect, the present invention relates to a method of identifying AFE mutants whose AMP-forming activities are insensitive to regulation by acetylation or deacetylation. The method involves providing cells that contain an AFE and an AFE acetylase but do not contain any functional AFE deacetylase, exposing the cells to conditions such that the activity of the AFE is essential for the survival of the cells, obtaining survived cells, and determining and comparing the amino acid sequence, the nucleotide sequence or both of the AFE in the survived cells to a wild-type sequence of the AFE. A polypeptide containing the amino acid sequence of a mutant protein identified by the method and a nucleic acid containing a nucleotide sequence that encodes the amino acid sequence are within the scope of the present invention. As shown in the examples below, an acetyl-CoA synthetase mutant insensitive to YFIQ regulation has been identified using the method described here. The mutated acetyl-CoA synthetase has a proline at residue position 641 while the wild-type protein has a leucine at that position.

The term "isolated nucleic acid" or "isolated polypeptide" used herein means a nucleic acid or polypeptide isolated from its natural environment or prepared using synthetic methods such as those known to one of ordinary skill in the art. Complete purification is not required in either case. The polypeptides and nucleic acids of the invention can be isolated and purified from normally associated material in conventional ways such that in the purified preparation the polypeptide or nucleic acid is the predominant species in the preparation. At the very least, the degree of purification is such that the extraneous material in the preparation does not interfere with use of the polypeptide or nucleic acid of the invention in the manner disclosed herein. The polypeptide or nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of clones, e.g., as these occur in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

In the specification and claims, the term "AMP-forming enzyme (AFE) acetylase" means bacterial YfiQ proteins and YfiQ structural and functional homologues in other prokaryotic and eukaryotic cells. Similarly, the term "AMP-forming enzyme (AFE) deacetylase" means bacterial CobB proteins and CobB structural and functional sirtuin homologues in other prokaryotic and eukaryotic cells.

The invention will be more fully understood upon consideration of the following non-limiting examples.

EXAMPLES

Investigations of Sirtuin-deficient Bacterial Strain

It had been previously demonstrated that sirtuin-deficient strains of *S. enterica* grow very poorly on propionate as a carbon and energy source, but the precise role of the sirtuin in the metabolic process remained unclear. We investigated whether eukaryotic sirtuins could compensate for the sirtuin deficiency in such stains. Plasmids carrying expression cassettes for human SIR2 genes were transformed into CobB-deficient *S. enterica* strains. The low-level expression of the human SIR2 protein restored growth of the bacteria on propionate. This result demonstrated the conservation of function of sirtuins among living organisms. By contrast, increased expression of the human sirtuin in the bacteria resulted in complete inhibition of growth.

Sirtuin deficient mutant strains were also unable to use acetate as a carbon and energy source. This was true in spite of the fact that the mutants carried a wild-type acs encoding the Acs enzyme. The wild-type bacterial strains grew well under similar conditions.

Other experiments, not reported in detail here, demonstrated that the low-affinity acyl kinase/phophotransacetylase system was functioning in these mutants to permit metabolism of acetate when present in high concentrations.

Sirtuin-dependent growth of *S. enterica* on acetate or propionate requires acetyl- or propionyl-CoA synthetase activity. It was important to determine whether sirtuin function was required for the synthesis of acyl-CoA via the low-affinity acyl kinase/phosphotransacetylase system, or via the high-affinity acyl-CoA synthetase-dependent pathway. Toward this end, genes encoding acyl-CoA synthetases capable of synthesizing propionyl-CoA (i.e., prpE, acs) (Horswill and Escalante-Semerena, 1999a) were inactivated in a strain carrying the wild-type cobB$^+$ allele. Strain JE4313 (cobB$^+$ μ1231acs prpE213::kan$^+$) grew very poorly on propionate (closed diamonds; doubling time=50 h), but this growth was reproducible. Inactivation of the pta gene in strain JE4313 completely blocked growth on propionate. Similar results were obtained when acetate was used as the sole source of carbon and energy. Unlike growth on propionate, however, growth of the acyl-CoA sythetase double mutant (prpE acs) on acetate was biphasic. The meaning of this behavior is unclear. These results indicated that sirtuin function was part of the high-affinity, acyl-CoA synthetase-dependent pathway of acyl-CoA synthesis.

In *S. enterica*, the lack of sirtuin or acyl-CoA synthetase (Acs/PrpE) activities result in a drastic decrease in the intracellular level of propionate or acetate. The intracellular level of acetate and propionate was measured to determine if the observed lack of growth on these SCFAs was due to insufficient levels of substrate for the acyl-CoA synthetases. The rate of intracellular accumulation of propionate in the sirtuin mutant was ca. 16-fold slower (0.93±0.22 nmol of propionate accumulated/mg of protein/min) than the rate measured in the sirtuin-proficient strain (14.84±0.50 nmol of propionate accumulated/mg of protein/min). An even more pronounced effect in the rate of propionate accumulation was measured in the strain lacking acyl-CoA synthetase activities (Acs, PrpE) (0.43±0.09 nmol of propionate accumulated/mg of protein/min). Similar results were obtained when acetate accumulation was assessed.

Sirtuin function is required for growth of *S. cerevisiae* on acetate or propionate. Sirtuin-deficient yeast strains have a growth defect on acetate containing medium. The yeast *S. cerevisiae* genome contains five sirtuins, SIR2 and HST1-4. We examined whether defects in SCFA metabolism were evident by examining the growth properties of yeast cells bearing mutations in SIR2 or its paralogues HST1, HST2, HST3, and HST4. The growth of these mutants was analyzed on rich (YP) medium containing various carbon and energy sources, including acetate and propionate. No defects were noted in any of the single mutants. However, quintuple sir2 hst1 hst2 hst3 hst4 mutant strains had significant growth defects on the SCFA-containing plates. These growth defects became worse as the concentration of SCFA increased (not shown). These defects appeared to be specific to SCFAs as no defects were seen when these strains were grown on glycerol/ethanol, another sub-optimal carbon and energy source.

Sirtuin function is required to activate acetyl-CoA synthetase (Acs) in *S. enterica*. Table 1 shows evidence of sirtuin-dependent control of acetyl-CoA synthetase activity. The activity of acetyl-CoA synthetase in a sirtuin-deficient strain was undetectable. A 42-fold increase in activity was observed when homogeneous CobB sirtuin was added to the reaction mixture. The fold further increased to 490-fold when excess NAD$^+$ was added to the sirtuin-containing reaction mixture. The level of acetyl-CoA synthetase activity obtained after treatment with CobB/NAD$^+$ was equivalent to the level of enzyme activity measured in cell-free extracts of the sirtuin-proficient strain. A control experiment with cell-free extract from a sirtuin-proficient strain carrying a deletion of the acs gene showed no detectable acetyl-CoA synthetase activity.

This data reported here supports the conclusion that in *S. enterica* sirtuin function is required for the activation of acetate and propionate via the high-affinity acyl-CoA synthetase-dependent pathway of acyl-CoA synthesis. The data presented in Table 1 are consistent with the conclusion that the activity of acetyl-CoA synthetase, and by extension propionyl-CoA synthetase, is controlled by their acetylation state. These data are consistent with the inability of sirtuin-deficient strains to use acetate or propionate as sources of carbon and energy. A role for sirtuins in short-chain fatty acid metabolism beyond activation is unlikely since the lack of sirtuin function was completely bypassed by increasing the level of activity of the low-affinity acyl kinase/phosphotransacetylase pathway of acyl-CoA synthesis. These results are consistent with the explanation that the lack of sirtuin function blocks the synthesis of short-chain fatty acyl-CoA, not its utilization. Since inactivation of the pta gene did not affect growth of the cobB+ acs+ and cobB+ prpE+ strains on acetate or propionate, it is concluded that the phosphotransacetylase (Pta) function is not part of the sirtuin-dependent pathway of short-chain fatty acid activation.

The involvement of sirtuins in short-chain fatty acid metabolism, in particular acetate metabolism, is of interest because of the prominent role of acetylated histones in eukaryotic chromatin silencing. An effective way of controlling the degree of histone acetylation, hence gene silencing, would be to control the level of substrate (i.e., acetyl-CoA) available to the acetyltransferase enzymes responsible for acetylating histones. This control of acetyltransferase activity could be afforded by modulating the activity of the acetyl-CoA synthetase enzyme. The data reported here are consistent with the hypothesis that acetylated short-chain fatty acyl-CoA synthetases (PrpE and Acs) are inactive, and that in the wild-type strain the deacetylase activity of sirtuins is responsible for keeping these enzymes active. It is also clear that in the absence of acetyl-CoA or propionyl-CoA synthetase activities, acetate and propionate are not retained inside the cell, suggesting that at low concentrations of these acids acyl-CoA synthetases are solely responsible for the accumulation of sufficient levels of these acids inside the cell to support growth.

TABLE 1

Sirtuin-dependent activation of acetyl-CoA synthetase (Acs) enzyme function

| Relevant genotype[a] | Omissions[b] | Additions | Acs Specific Activity[c] |
|---|---|---|---|
| Acs+ cobB+ | None | | 460 ± 0.057 |
| | Mg(II)/ATP | | 95 ± 0.014 |
| | Coenzyme A | | <1 |
| Acs+ cobB− | None | | <1 |
| | None | 10 µg CobB | 42 ± 0.027 |
| | None | 10 µg CobB + NAD+ | 490 ± 0.070 |
| | Coenzyme A | 10 µg CobB + NAD+ | <1 |

[a]All S. enterica strains also carried metE205 ara-9 ack101::MudJ mutations in the genome.
[b]The complete reaction mixture contained: coenzyme A, Mg/ATP, and crude cell-free extract obtained from a strain with the indicated genotype.
[c]Specific activity is defined as pmoles of acetyl-CoA formed min$^{-1}$ mg of protein$^{-1}$. Results are the average of three independent determinations.

Sir2-Dependent Activation of Acetyl-Coenzyme A Synthetase by Deacetylation of an Active Site Lysine Residue Materials and Methods Cloning of the acs gene: The wild-type acs gene was amplified from the S. enterica genome, using primers containing a 5'-NdeI site (5'-GAGAACAACCATATGAGCCAAACA-CAT-3', SEQ ID NO:3), and a 3'-SapI site (5 '-AAC-CCCGCTCTTCCGCATGACGGCATCGCGATGGC-3', SEQ ID NO:4). The ~2.0 kb product was gel purified, and cloned into the pGEM®-T Easy vector (Promega, Madison, Wis. as per manufacturer's directions. This vector was cut with NdeI and SapI restriction enzymes, and the 2.0 kb acs+ fragment was gel purified, and ligated into plasmid pTYB1 (New England Biolabs, Beverly, Mass.), which had been cut with the same enzymes. The resultant 9.5-kb plasmid was named pACS10, and was used for the overexpression of Acs protein for chitin-affinity purification.

Overexpression and purification of Acs proteins: Plasmid pACS10 was introduced into either cobB+, or cobB− S. enterica strains containing plasmid pTara, which allows the induction of the T7 RNA polymerase via addition of arabinose (16). Strains containing both plasmids were grown overnight in Luri-Bertani broth at 37° C., and then subcultured (1:200, v:v) into 2 L No-Carbon E (NCE) medium (17), supplemented with 30 mM succinate, 1 mM MgSO$_4$, 0.5 mM L-methionine, and 5 mM glucose, to repress the expression of the T7 RNAP during growth. This culture was grown at 30° C., with vigorous shaking. At an OD$_{600}$ of 0.3, L-arabinose was added to a final concentration of 0.05% (w/v). The culture was allowed to grow overnight at 30° C. The cells were harvested, then disrupted with 2 passes at 1.26 Kpa using a French pressure cell (Spectronic Instruments, Inc. Rochester, N.Y.). Cellular debris was removed from the lysate via centrifugation at 39,000×g for 45 min at 4° C. using an Avanti™ J-251 refrigerated centrifuge (Beckman Coulter, Fullerton, Calif.) equipped with a JA 25.50 rotor. Overexpressed Acs was purified from these cell-free extracts via chitin-affinity chromatography, as per the manufacturer's directions (NEB, Beverly, Mass.). The purified Acs was then dialyzed into storage buffer: 0.05 M 4-(2-hydroxyethyl)-1-piperazineethanesulfonic acid (HEPES), 0.1 M KCl, pH 7.5, containing 2.2 M glycerol. This protein was then drop-frozen into liquid nitrogen, and stored at −80° C.

Immublot analysis: Approximately 7.5 µg of purified Acs protein obtained from cobB− cells was incubated with 2 µg purified CobB sirtuin in a 100-µL reaction mixture containing 25 mM Tris-Cl (tris(hydrohxymethyl)aminomethane-chloride) buffer pH 8.0, 50 mM NaCl, 200 µM ethylenediaminetetraacetate (EDTA), and 200 µM NAD+. Samples (20 µl) were removed at various time points during the incubation at 37° C. Immunoblotting of Acs protein was carried out on 1.5 µg samples of protein with or without pretreatment with purified CobB sirtuin as indicated. The samples were separated by electrophoresis on 4-15% SDS/PAGE gels and then transferred semidry on a Bio Rad SD device (Bio Rad Laboratories) for 35 min at 10 V to a PVDF membrane. The membrane was preincubated for 25 min in 1X PBST (phosphate buffered saline plus 0.5% Triton X-100) containing 3% NFDM (nonfat dry milk). Primary rabbit anti-acetyl-lysine antibody (lot #19212, Upstate Biotechnology, NY) was diluted 1:1000 in PBST/3% NFDM and incubated at room temperature for 3 h. The blot was washed with H$_2$O and incubated with secondary anti-rabbit antibody (Pharmacia) diluted 1:3000 in PBST/3% NFDM for 1.5 h at room temperature. The blot was washed in H$_2$O for 20 min, and in PBST for 20 min, then washed with water four times before exposure with ECL Plus (Pharmacia) according to the manufacturer's instructions.

NAD+_, CobB-dependent activation of acetyl-CoA synthetase: Acs$^{4c}$ protein (150 ng) was incubated at 37° C. with 1 mM NAD+ and varying levels of CobB (0-10 µg) in 50 mM HEPES buffer pH 7.5, 200 µM TCEP-HCl (Tris(2-carboxyethyl)phosphine hydrochloride) for 30 min. The acyl-CoA synthetase reaction was started with the addition of 100 µM radiolabeled [1-$^{14}$C] acetate, 1 mM Mg(II)/ATP, and 1 mM coenzyme A in 50 mM HEPES pH 7.5, 200 µM TCEP-HCl, bringing the total reaction volume to 100 µl. The reaction continued incubation at 37° C. for one additional hour. The reaction was terminated with the addition of 20 µl 1 M formic acid. The reaction product, acetyl-CoA, was isolated and quantified as previously reported (5). To show dependence on NAD+, the level of this compound varied from 0-1 mM in the reaction mixture.

Peptide fingerprinting: Isolated Acs and Acs$^{Ac}$ proteins were digested with trypsin (Promega Corp., Madison, Wis.) at a ratio of 1:20000 (tryspin:protein) in 20 mM ammonium bicarbonate, pH 8 at 37° C. overnight. Proteolytic peptides were analyzed by matrix-assisted laser desorption ionization time-of-flight (MALDI-TOF) on a Voyager DE STR (Applied Biosystems, Foster City, Calif.). Non-redundant and Salmonella databases were searched using Protein Prospector (UCSF, prospector.ucsf.edu). Peptide sequence of 367.2 [M+2H+]$^{2+}$ ion was confirmed by mass spectrometry analysis of peptide fragments from collision-induced dissociation (CID). Peptides were desalted using C18 Ziptips (Millipore, Billerica, Mass.) into 50% (v/v) methanol and 5% (v/v) formic acid. Desalted peptides were nanosprayed through a 1 μm silver-coated PicoTip (New Objective, Woburn, Mass.) directly into a QSTAR Pulsar quadrupole orthogonal TOF tandem mass spectrometer (Applied Biosystems/MDX Sciex, Foster City, Calif.), equipped with a Protana XYZ manipulator source (MDS Protana A/S, Odense, Denmark). Fragmentation spectra were obtained in Product mode with 2 sec CID acquisitions at 30V collision energies. Errors on fragmentation ions were less than 0.01 amu. Non-redundant and *Salmonella* databases were searched using Mascot (www.matrixscience.com).

Results

Members of the Sir2 family of proteins (i.e., sirtuins) are NAD+-dependent deacetylase enzymes involved in chromosome stability, gene silencing and cell aging in eukaryotes and archaea (1-3). All previously known substrates of sirtuins are components of chromatin and/or affect gene transcription. Strains of the enterobacterium *S. enterica* lacking sirtuin (encoded by the cobB gene) cannot grow on propionate and low acetate as carbon and energy sources because the acyl-CoA synthetases responsible for the conversion of free acids into acyl-CoA derivatives are inactive (4, 5). Our work shows that acetyl-CoA synthetase activity (FIG. 1A; encoded by the acs gene) is regulated by post-translational acetylation. We also show that activation of acetylated Acs requires CobB deacetylase activity.

Acs enzyme synthesized by a cobB− strain of *S. enterica* was inactive in crude cell-free extract (5). To address the possibility that Acs activity was post-translationally regulated, the acs gene of *S. enterica* was overexpressed in cobB+ or cobB− strains, and the protein was purified. Acs protein produced by the cobB− strain was >100-fold less active than protein isolated from the cobB+ strain (Table 1). Incubation of inactive Acs enzyme with purified CobB and NAD+ resulted in a 480-fold increase in Acs activity; the reaction was NAD+ dependent (Table 2). The increase in Acs activity measured in the presence of CobB and absence of NAD+ was also observed when bovine serum albumin substituted for CobB, thus this effect appears to be due to nonspecific stabilization of Acs. We hypothesized that the CobB-dependent activation of Acs was due to the removal of acetyl groups from the inactive form of the enzyme. We took two approaches to determine the chemical nature of the modification, and the site of modification in Acs.

TABLE 2

NAD+-, CobB-dependent activation of acetyl-CoA synthetase. Overexpression Host Genotype$^a$

| CobB+ | | CobB− | |
|---|---|---|---|
| Additions$^b$ | Acs Sp. Act.$^c$ | Additions$^b$ | Acs Sp. Act$^c$ |
| None | 119 ± 5 | None | Not detectable |
| BSA$^d$ | 351 ± 14 | BSA | 9 ± 0.1 |
| CobB | 806 ± 9 | CobB | 22 ± 4 |
| CobB, BSA | 810 ± 4 | CobB, BSA | 19 ± 4 |
| CobB, NAD+ | 809 ± 8 | CobB, NAD+ | 480 ± 4 |
| BSA, CobB, NAD+ | 902 ± 10 | BSA, CobB, NAD+ | 483 ± 19 |

$^a$The relevant genotype of the strain from which the Acs protein was purified.
$^b$All reaction mixtures contained coenzyme A, Mg(II)/ATP, and Acs proteins.
$^c$Specific Activity is defined as nmoles of acetyl-CoA formed min$^{-1}$ mg$^{-1}$. Results are the average of three independent determinations.
$^d$BSA, bovine serum albumin.

Immunoblot analysis was performed to determine whether lysyl residues were acetylated in inactive Acs enzyme. Polyclonal anti-acetyl-lysine Ab reacted strongly with Acs enzyme isolated from a cobB− strain (FIG. 1B); in contrast, the same Ab lacked detectable reactivity with Acs isolated from a cobB+ strain (FIG. 1B). The decreased reactivity of Acs with the antibody was dependent on the presence of NAD+ and CobB in a time-course experiment, establishing a correlation between the lack of Acs activity and acetylation.

The acetylation site on inactive Acs enzyme was mapped by comparing peptide masses generated from tryptic digests of Acs protein isolated from cobB+ and cobB− cells by MALDI-TOF analysis of intact Acs and Acs$^{Ac}$ proteins. Mass difference between intact Acs and Acs$^{Ac}$ proteins was determined to be at least one acetyl group. Acs proteins isolated from over-expressed in cobB+ (A) or cobB− (B) cells were co-crystallized in 2,5-dihydroxybenozic acid (DHB) and analyzed by MALDI-TOF. Multiple charged species of these proteins are indicated. Masses calibrated against a bovine serum albumin (BSA) standard and are within 200 ppm error. The proteolytic mass fingerprints represented >74% of the amino acid sequence from Acs. The mass fingerprints for both active, deacetylated Acs and inactive, acetylated Acs (Acs$^{Ac}$) were virtually identical in peptide masses and their relative intensities, except for a 733.4 ion. This singly-charged ion was qualitatively more abundant in the Acs$^{Ac}$ preparation than in the Acs preparation and corresponds to the predicted mass of the $^{607}$SGK$^{AC}$IMR$^{612}$ (SEQ ID NO:5) peptide with acetylation of residue Lys609. Acetylation of Lys6O9 was confirmed by fragmenting the 367.2 ion (the doubly-charged species of the 733.4 ion) in Acs or AcsAc tryptic digests. A search of the nonredundant protein database yielded a single hit with the sequence $^{607}$SGK$^{AC}$IMR$^{612}$ (SEQ ID NO:5) from *S. enterica* Acs with a 0.01 amu error on the peptide mass and <21 ppm error on the peptide fragment masses (Table 3). Fragmentation occurs primarily at the peptide bond and yields a b-series of ions with the charge on the N-terminal amino acid and a y-series of ions with the charge on the C-terminal amino acid. All but two of the major fragmentation ions present in the fragmentation mass spectra of the 367.2 ion were readily assigned to the $^{607}$SGK$^{AC}$IMR$^{612}$ (SEQ ID NO:5) sequence. Most notably, both the y1 to y5 and b2 to b4 fragment ions were present. These ions span the acetylated Lys609 residue, unambiguously identifying the site of acetylation. These results show that Acs protein overproduced by the cobB− strain contains acetyl-lysine at residue Lys609.

TABLE 3

Tandem mass spectrometry analysis of the acetylated peptide of Acs

| b-Series, m/z[1] | Observed m/z | Sequence | y-Series, m/z[2] | Observed m/z | Sequence |
|---|---|---|---|---|---|
| — | — | — | y6 - 733.403 | — | SGK$^{Ac}$IMR (SEQ ID NO: 5) |
| b1 - 88.040 | — | S | y5 - 646.371 | 646.368 | GK$^{Ac}$IMR (SEQ ID NO: 8) |
| b2 - 145.061 | 145.060 | SG | y4 - 589.350 | 589.349 | K$^{Ac}$IMR (SEQ ID NO: 9) |
| b3 - 315.167 | 315.166 | SGK$^{Ac}$ | y3 - 419.244 | 419.242 | IMR |
| b4 - 428.251 | 428.244 | SGK$^{Ac}$I (SEQ ID NO: 6) | y2 - 306.160 | 306.157 | MR |
| b5 - 559.291 | — | SGK$^{Ac}$IM (SEQ ID NO: 7) | y1 - 175.119 | 175.118 | R |
| b6 - 715.393 | — | SGK$^{Ac}$IMR (SEQ ID NO: 5) | — | — | — |

[1]Predicted fragment ion masses of SGK$^{Ac}$IMR (SEQ ID NO: 5) with the charge on the N-terminal amino acid; K$^{Ac}$, acetyl-lysine.
[2]Predicted fragment ion masses of SGK$^{Ac}$IMR (SEQ ID NO: 5) with the charge on the C-terminal amino acid.

To investigate whether acetylation affected both reactions catalyzed by Acs, we took advantage of knowledge that Acs can synthesize propionyl-CoA from propionate (6). Propionyl-AMP (7, 8) was provided as substrate in a reaction mixture containing CoA and Acs or Acs$^{Ac}$. Acs$^{Ac}$ enzyme was as efficient (sp. act.=107 μmol product/min/mg of protein), if not more efficient than the Acs enzyme (sp. act.=73 μmol product/min/mg of protein) in generating propionyl-CoA from propionyl-AMP and CoA. No product was detected in the absence of CoA. These results show that the thioester-forming activity of Acs$^{Ac}$ remains unaffected by acetylation, and indicate that acetylated residues in Acs$^{Ac}$ do not affect the thioester-forming activity of the enzyme. Acetylation of the active site Lys609 of Acs has the same effect on Acs activity as substitutions of Lys592 have on propionyl-CoA synthetase activity (8). Lys609 of Acs is an invariant residue of a conserved motif in the family of AMP-forming enzymes (FIG. 3). Lys592 of propionyl-CoA synthetase, Lys529 of luciferase, and Lys517 of gramicidin synthetase 1 (equivalent to Lys609 of Acs) are essential for the synthesis of the corresponding AMP reaction intermediate, but not for the thioester-forming activity of these enzymes (8-11). We believe that acetylation modulates the activity of all the AMP-forming family of enzymes.

These data provide evidence for a broadened role of sirtuins in cell physiology that includes intermediary metabolism. Our results suggest a mechanism for linking the physiological state of the eukaryotic cell with the acetylation state of histones, a key factor in chromatin silencing and chromosome stability. Several studies implicate sirtuins in yeast and metazoans in lifespan control (12, 13). Similarly, manipulation of NAD$^+$ biosynthetic mechanisms has been shown to affect lifespan (14). A recent study documenting the effect of caloric restriction on yeast mother cell longevity suggested that the increased longevity was causally associated with increased respiration; this lifespan extension was sirtuin dependent (15). As the Acs enzyme produces acetyl-CoA, a key metabolite of the Krebs cycle, Acs may represent a target for lifespan extension.

Isolation of Gene Encoding Acetyltransferase (yfiQ)

*S. enterica* strain JE2845 (cobB1206::MudJ) was transduced to tetracycline resistance with a bacteriophage P22 lysate grown on a pool of ca. 80000 colonies, each carrying an independent, random insertion of the defective transposable element Tn10d(Tc). After tetracycline selection, plates were replica printed to NCE minimal medium plates supplemented with 10 mM acetate as the sole carbon and energy source. These plates were incubated at 37° C. for 48 hours. Colonies which were able to utilize 10 mM acetate as the sole carbon and energy source were then picked, and restreaked to acetate plates. After an additional 48 hours, colonies which continued to grow on acetate were replica printed onto plates containing either tetracycline or kanamycin, to determine whether the original drug resistance cassettes were present. Of the seventeen acetate-utilizing strains isolated only one strain retained the kanamycin-resistant MudJ in cobB. Arbitrary primer sequencing determined that the Tn10d(Tc) was located in an ORF designated yfiQ.

Sequence obtained from left side of insertion element is: AGCCACCTTTTTGGGNAACCG-GCGGGGNNTTANGGNCANACAANNNGGG NTTTG-NACCAGCAAACCGNGAATCCGCGCT-TGCGGCCAGGCCATCTTTAC ACGATCAAAAATAGCGTTCGCGGCCTGT-TGTACCTCGCTTGCGGTCCGCA GGTAAAGCATGAC-CCCCTGAACTTCAGATTTATGCGGAAT-GTCGGGCGAG CGCANCCTTGAGAGCTACCGGATAGC-CNANCNGNTTTTTTTTTTT (SEQ ID NO:10); sequence obtained from the right side of insertion element is: AGCTTTTNGNTNCCGACAGGTNNGNGGC-NGCGTCATCNTGTNAATGCCAT GGACNANATGCG-TAGGCGCGNANGAGCTTCGTGTGGTGGT-NGATCACTAT CCAGTNCNTGATGNTTNTCCTNNANAT-GATGNGAANNCNCNNACAANNTT (SEQ ID NO:11). A BLAST search showed that the sequences matched segments of GenBank No. AE008820 (yfiQ). FIG. 4 shows the complete coding sequence of *Salmonella typhimurium* yfiQ. The segments that matched the sequences obtained from the left and right side of insertional element are highlighted. The insertional element is presumed to be between the highlighted segments.

Isolation of Acetylation-Resistant Acs (L641P): Construction of pACS8

Plasmid pACS7 (wild-type acs cloned into pBAD30) was introduced into the mutator strain XL-1 Red (Stratagene, La Jolla, Calif.), and prepped after 2 subcultures. This plasmid pool was electroporated into strain JE6668 (acs prpE pta cobB), and colonies were selected that could utilize 10 mM acetate, in a CobB-independent fashion. Plasmids were isolated from colonies isolated in this selection, and all contained a single point mutation (T to C), which generates L641P in the Acs protein. This point has been reconstructed in a site-directed manner, and this single mutation is sufficient for this acetylation-resistant phenotype of Acs.

Figure 5:
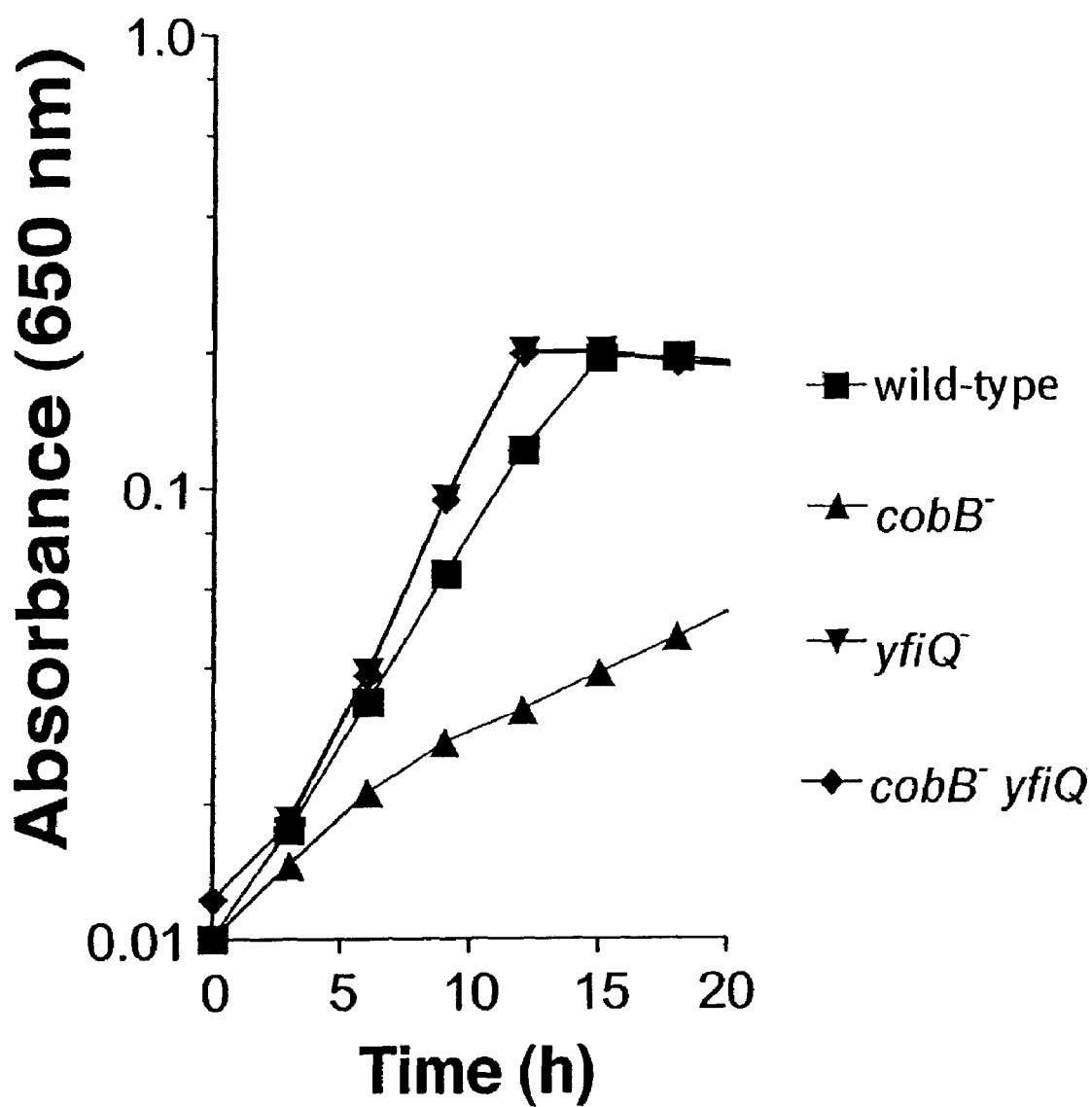
FIG. 5 shows that acetyl-coA synthetase (Acs) activity can be restored in sirtuin-deficient strains of *S. enterica* via disruption of the gene yfiQ.

Disruption of yfiQ Function Restored Growth of a Sirtuin-Deficient Strain (cobB⁻) on Acetate As shown in FIG. 5, the strains indicated therein were grown in minimal NCE salts supplemented with 10 mM acetate as the sole carbon and energy source. Growth behavior of the strains under these conditions represents Acs activity. The wild-type growth (wild-type Acs activity) is represented by the squares. The no growth (and no Acs activity) control is represented by the sirtuin-deficient strain (cobB⁻), and shown as dark triangles. Disruption of yfiQ in the cobB⁻ background restored growth, and Acs activity (diamonds, behind light inverted triangles).

The present invention is not intended to be limited to the foregoing examples, but encompasses all such modifications and variations as come within the scope of the appended claims.

REFERENCES

1. C. B. Brachmann et al., *Genes and Dev.* 9, 2888-2902 (1995).
2. D. Moazed, *Curr Opin Cell Biol* 13, 232-238 (2001).
3. S. D. Bell, C. H. Botting, B. N. Wardleworth, S. P. Jackson, M. F. White, *Science* 296, 148-151 (2002).
4. A. W. Tsang, J. C. Escalante-Semerena, *J. Bacteriol.* 178, 7016-7019 (1996).
5. V. J. Starai, H. Takahashi, J. D. Boeke, J. C. Escalante-Semerena, *Genetics* 163, 545-555 (2003).
6. A. R. Horswill, J. C. Escalante-Semerena, *Microbiology* 145, 1381-1388 (1999).
7. P. Berg, *J. Biol. Chem.* 222, 991-1013.(1956).
8. A. R. Horswill, J. C. Escalante-Semerena, *Biochemistry* 41, 2379-2387 (2002).
9. Y. Lee, F. S. Esch, M. A. DeLuca, *Biochemistry* 20, 1253-1256 (1981).
10. B. R. Branchini, M. H. Murtiashaw, R. A. Magyar, S. M. Anderson, *Biochemistry* 39, 5433-5440 (2000).
11. E. Conti, T. Stachelhaus, M. A. Marahiel, P. Brick, *EMBO J.* 16, 4174-4183. (1997).
12. S. J. Lin, P. A. Defossez, L. Guarente, *Science* 289, 2126-2128 (2000).
13. H. A. Tissenbaum, L. Guarente, *Nature* 410, 227-230 (2001).
14. R. M. Anderson et al., *J Biol Chem* 277, 18881-18890 (2002).
15. S. J. Lin et al., *Nature* 418, 344-348 (2002).
16. D. R. Wycuff, K. S. Matthews, *Anal Biochem* 277, 67-73 (2000).
17. D. Berkowitz, J. M. Hushon, H. J. Whitfield, J. Roth, B. N. Ames, *J. Bacteriol.* 96, 215-220 (1968).

We claim:

1. A method for modulating the activity of *Salmonella enterica* acetyl-CoA synthetase comprising the step of introducing a substitution mutation into amino acid position 641 of the *Salmonella enterica* acetyl-CoA synthetase protein amino acid sequence defined by SEQ ID NO:24, wherein the mutation renders acetyl-CoA synthetase acetylation resistant.

2. The method of claim 1, wherein leucine at amino acid position 641 is substituted with a proline.

* * * * *